United States Patent [19]

Greenwald et al.

[11] Patent Number: 5,622,986

[45] Date of Patent: Apr. 22, 1997

[54] 2'-AND/OR 7-SUBSTITUTED TAXANES

[75] Inventors: Richard B. Greenwald, Somerset; Durgadas Bolikal, Edison, both of N.J.

[73] Assignee: Enzon, Inc., Piscataway, N.J.

[21] Appl. No.: 351,462

[22] PCT Filed: Oct. 19, 1994

[86] PCT No.: PCT/US94/12133

§ 371 Date: Dec. 12, 1994

§ 102(e) Date: Dec. 12, 1994

[87] PCT Pub. No.: WO95/11020

PCT Pub. Date: Apr. 27, 1995

Related U.S. Application Data

[63] Continuation-in-part of Ser. No. 140,346, Oct. 20, 1993, abandoned.

[51] Int. Cl.⁶ .................. A61K 31/335; C07D 305/14
[52] U.S. Cl. ................ 514/449; 549/510; 549/511
[58] Field of Search ................... 549/510, 511; 514/449; 528/421

[56] References Cited

U.S. PATENT DOCUMENTS

| | | | |
|---|---|---|---|
| 4,101,380 | 7/1978 | Rubinstein et al. | 195/63 |
| 4,179,337 | 12/1979 | Davis et al. | 435/181 |
| 4,275,000 | 6/1981 | Ross | 260/112 R |
| 4,534,899 | 8/1985 | Sears | 260/403 |
| 4,582,805 | 4/1986 | Bozzelli et al. | 435/180 |
| 4,680,338 | 7/1987 | Sundoro | 525/54.1 |
| 4,814,470 | 3/1989 | Colin et al. | 514/449 |
| 4,847,325 | 7/1989 | Shadle et al. | 525/54.1 |
| 4,904,582 | 2/1990 | Tullis | 435/6 |
| 4,942,184 | 7/1990 | Haugwitz et al. | 514/449 |
| 4,943,579 | 7/1990 | Vishnuvajjala et al. | 514/283 |
| 4,960,790 | 10/1990 | Stella et al. | 514/449 |
| 5,004,758 | 4/1991 | Boehm et al. | 514/283 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,091,176 | 2/1992 | Braatz et al. | 424/78.17 |
| 5,122,614 | 6/1992 | Zalipsky | 548/520 |
| 5,136,060 | 8/1992 | Holton | 549/510 |
| 5,157,049 | 10/1992 | Haugwitz et al. | 514/449 |
| 5,227,400 | 7/1993 | Holton et al. | 514/444 |
| 5,229,526 | 7/1993 | Holton | 549/213 |
| 5,272,171 | 12/1993 | Ueda et al. | 514/449 |
| 5,278,324 | 1/1994 | Kingston et al. | 549/510 |
| 5,342,947 | 8/1994 | Lackey et al. | 546/41 |
| 5,352,805 | 10/1994 | Kingston et al. | 549/510 |
| 5,362,831 | 11/1994 | Mongelli et al. | 526/304 |

FOREIGN PATENT DOCUMENTS

| | | |
|---|---|---|
| 0510356 | 3/1992 | European Pat. Off. |
| 0524093 | 7/1992 | European Pat. Off. |
| 0524093 | 1/1993 | European Pat. Off. |
| 91/02763 | 3/1991 | WIPO |
| 9324476 | 12/1993 | WIPO |

OTHER PUBLICATIONS

Mathew et al, "J. Med. Chem.," vol. 35, No. 1, pp. 145–151, 1992.
Nathan et al, "Polymer Preprints", vol. 31, pp. 213–214. 1990.
Zalipsky et al, "Eur. Polym. J.", vol. 19, No. 12, pp. 1177–1183, 1983.
Weiner et al, "J. Med. Chem.", vol. 16, No. 5, pp. 573–574, 1973.
Cecchi et al, "J. Med. Chem.", vol. 24, No. 5, pp. 622–625, 1981.
Angew, Chem. Int. Ed. Engl, (1994), 33, No. 1516, K.C. Nicolaou, et al.
Bioorganic & Medicinal Chemistry Letters, vol. 4, No. 20, pp. 2465–2470, (1984), Richard B. Greenwald, et al.
Proc. Int. Symp. Control. Release Bioact. Mater., 21 (1994) #1381, Yuichi Ohya, et al.
Cancer Treatment Reviews (1990), 17, 127–131, Terrence W. Doyle, et al.
Bioorganic & Medicinal Chemistry Letters, vol. 4, No. 18, pp. 2223–2228 (1994) Shu–Hui Chen, et al.
Journal of Pharmaceutical Sciences, vol. 83, No. 4, Apr. 1994, Tetsuiji Yamaoka, et al.
Clinical Pharmacy, vol. 8, Apr. 1989, pp. 274–293, Ronald A. Fleming, et al.
Oncology, Dec. 1992, pp. 17–23, Michael J. Hawkins, et al.
Biotechnology and Applied Biochemistry 9, 258–268 (1987).
Journal of Controlled Release, 10 (1989) 145–154.
Polymer Bulletin 18, 487–493 (1987).
Ouchi et al, Drug Design & Discovery, vol. 9, pp. 93–105, (1992).
Nicolaou, Nature, vol. 364, pp. 464–466, 29 Jul. 1993.
Commercon et al, Tetrahedron Letters, vol. 33, No. 36, pp. 5158–5188 (1992).
Magre et al, J. Org. Chem., vol. 51, pp. 797–802 (1986).
Gueritte–Voegelein et al, J. Med. Chem., 34, pp. 992–998 (1991).

Primary Examiner—Ba K. Trinh
Attorney, Agent, or Firm—Michael N. Mercanti

[57] ABSTRACT

2'- and/or 7'- substituted taxoid derivatives having improved water-solubility and/or enhanced therapeutic activity and methods of making the same are disclosed.

27 Claims, No Drawings

2'-AND/OR 7-SUBSTITUTED TAXANES

This application is a continuation-in-part of U.S. patent application Ser. No. 08/140,346 filed Oct. 20, 1993, now abandoned and is a 371 application of PCT/US94/12133 dated Oct. 19, 1994.

TECHNICAL FIELD

The present invention relates to compounds having anti-microtubule activity. In particular, the invention relates to taxoid-based derivatives which demonstrate prolonged anti-neoplastic activity and/or improved water-solubility.

BACKGROUND OF THE INVENTION

Taxol, or paclitaxel as it is sometimes called, has been investigated as an anti-cancer agent. Taxol is a plant product derived in minute quantities from the needles and bark of the western pacific yew, *Taxus brevifolia*. In chemotherapy, taxol is known as an anti-microtubule agent and is thought to inhibit cell mitosis through the enhancement of the rate of microtubular assembly and prevention of microtubular depolymerization. Numerous studies indicate that the agent has activity against several malignancies. To date, its use has been severely limited by, among other things, its short supply, poor water solubility and immunogenicity.

The pacific yew is a rare, slow-growing tree which is not typically cultivated. In addition, the anti-neoplastic portions of the tree are very minute. Extraction of these portions is complicated and costly. One solution to the problem of short supply has been suggested in U.S. Pat. No. 5,019,504 which discloses an artificial media for producing certain desirable alkaloids. Alternatively, synthetic derivations such as taxotere and taxol intermediates have also been reported. See, for example, U.S. Pat. No. 5,015,744.

Hypersensitivity reactions from taxol administration are known. See, for example, *J. Clin. Oncol.* 8:1263–1268 (1990). Indeed, since taxoids are usually extracted from a natural plant source, some hypersensitivity is expected. Moreover, certain non-aqueous vehicles which have been used to overcome the water solubility problems of taxol have also been implicated in causing hypersensitivity reactions.

Although taxoids hold promise as therapeutic agents, there is a need to provide taxoid-based derivatives which are more water soluble and/or are more active against a wider range of virulent neoplasms than taxol.

SUMMARY OF THE INVENTION

The present invention is generally directed to 2'- and/or 7-substituted taxoid-based compositions, methods of their preparation and use in mammals. The inventive compositions include a taxoid substituted in at least one of the 2'- and 7- positions with a moiety of Formula (I):

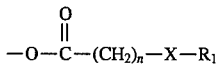

wherein:
n=zero or a positive integer, preferably one;
X=oxygen or NL, where L is selected from the group consisting of hydrogen, $C_{1-8}$ alkyls, aryls and aralkyls; and
$R_1$=a group which enhances the water solubility and/or therapeutic activity of the composition when compared to the unmodified taxoid. $R_1$ represents moieties capable of forming polymeric esters, simple or polymeric carbonates.

Such moieties can include functionalized, substantially nonantigenic polymers, substituted or unsubstituted $C_{1-12}$ alkyls. $R_1$ preferably includes an alkyl-terminated polyalkylene oxide such as monomethoxy polyethylene glycol, (mPEG). These aspects provide compositions such as taxoid-7-carbonates, 2'- taxoid-PEG-esters and/or simple taxoid-7-carbonates in combination with 2'-PEG esters. Another particularly preferred aspect of the invention is where (n) is one and $R_1$ includes a polyethylene glycol.

The invention thus includes the following types of taxoid-based compositions:
  i) 7-carbonates; 2'-carbonates;
  ii) 7-polymeric esters; 2'-polymeric esters;
  iii) 2'-polymeric ester-7-carbonates;
  iv) 2',7-disubstituted polymeric esters; 2',7-disubstituted carbonates; and
  v) combinations thereof.

In those aspects of the invention where the taxoid is disubstituted, it is to be understood that the moieties included in the 2' and 7 position need not be the same; bis-substituted taxoids, however, are within the scope of the invention.

Methods of making and using the compositions described herein are also provided.

DETAILED DESCRIPTION OF THE INVENTION

A. INTRODUCTION

The taxoid-based compositions of the present invention contain substituents in the 2' and/or 7 positions of the taxoid. These substitutions enhance water solubility and/or improve therapeutic activity when compared to unmodified compositions.

B. TAXOIDS and TAXOID DERIVATIVES

For purposes of the present invention, the term "taxoid" includes all compounds within the taxane family of terpenes. Thus, taxol (paclitaxel), 3'-substituted tert-butoxy-carbonyl-amine derivatives (taxoteres) and the like as well as other analogs available from, for example, ESCAgenetics of San Carlos, Calif. are within the scope of the present invention.

Taxol has the following structure:

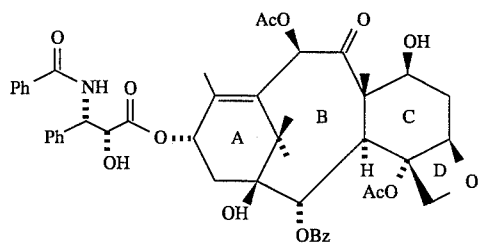

Throughout the disclosure, the invention is described with reference to taxol for illustrative purposes. It is to be understood that the modifications described herein are suitable for all taxoids and related molecules. The only limitation on this provision is that the selected taxoid must be capable of undergoing at least one of the 2' and/or 7 position modifications described herein. Taxol, however, is a preferred taxoid.

C. 2' AND 7 POSITION SUBSTITUENTS

The substituents included in 2'- and/or 7-substituted taxoid-based compositions of the present invention are set forth below as formula (I):

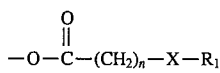

wherein:

(n)=zero or a positive integer;

X=preferably oxygen, although X can also=NL, where L is selected from the group consisting of hydrogen, $C_{1-8}$ alkyls, aryls and aralkyls; and $R_1$=a group which enhances at least one of the properties of water solubility and therapeutic activity of the composition when compared to the unsubstituted taxoid.

The compositions of the present invention are described as being 2'- and/or 7-position carbonates when (n) is zero or 2' and/or 7 position polymeric esters when (n) is a positive integer. Preferably, (n) is zero or one.

$R_1$ includes substituents such as:

a) substantially nonantigenic polymers which have been suitably functionalized or activated for attachment to the taxoid via the linking portion of (I) or (I'), which is:

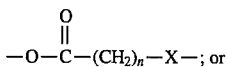

b) $C_{1-12}$, and preferably $C_{1-4}$ alkyls or substituted alkyls. The substituted alkyls can include one or more hydroxy, amino, alkylthio, aryl and aralkyl moieties. These are examples of simple carbonate substituents.

D. $R_1$ SUBSTANTIALLY NONANTIGENIC POLYMERS

In the situations where $R_1$ includes substantially nonantigenic polymers, such as polyalkylene oxides (PAO's), mono-activated, alkyl-terminated PAO's such as monomethyl-terminated polyethylene glycols (mPEG's) are preferred; bis-activated polyethylene oxides are also contemplated for purposes of cross-linking taxoids or providing a means for attaching other moieties such as targeting agents. For example, the homobifunctional bis succinimidyl carbonate of PEG disclosed in U.S. Pat. No. 5,122,614 or any other alpha, omega homo-substituted polymer can be used. Moreover, heterobifunctional polymers are also contemplated.

Although polyethylene glycols vary substantially by weight, polymers having molecular weight ranges of from about 200 to about 10,000 are usually selected for the purposes of the present invention. Molecular weights of from about 1,000 to about 7,500 are preferred and 2,000 to about 5,000 are particularly preferred.

In certain aspects of the invention, however, particularly when the 2' position of the taxoid is substituted with a polymeric ester, the molecular weight of the polymers selected is from about 20,000 to about 80,000. Polymers of from about 30,000 to about 50,000 are preferred, and polymers of about 35,000 to about 45,000 are especially preferred.

The polymeric substances included herein are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers maintained. In addition to MPEG, $C_{1-4}$ alkyl- terminated polymers are also useful.

As an alternative to PAO-based polymers, effectively non-antigenic materials such as dextran, polyvinyl pyrrolidones, polyacrylamides, polyvinyl alcohols, carbohydrate-based polymers and the like can be used. Those of ordinary skill and the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immunogenic response in mammals.

In this aspect of the invention, the taxoid-polymer conjugates retain at least a substantial portion of the bioactivity of the taxoid moiety prior to conjugation. For purposes of the present invention, the term "substantial portion of the activity" means that at least some therapeutic effectiveness is maintained. In any event, the advantageous properties of higher aqueous solubility, substantially longer circulating life and reduced antigenicity, either alone or in combination outweigh decrease, if any, of taxoid activity.

E. $R_1$ CARBONATE FORMING MOIETIES

As stated above, when (n) is a positive integer, carbonates are formed in either or both of the 2' and 7 positions of the taxoid. One particularly preferred taxoid includes a 7-methyl carbonate moiety. Other simple 7-position carbonates containing alkyl or aralkyl moieties are possible using $C_{1-2}$ and preferably $C_{1-4}$ alkyl or substituted alkyl groups within the reagents of Formula (IV) which is described in Section G.

F. SYNTHESIS OF 2' AND/OR 7 SUBSTITUTED TAXOIDS

The compounds of the present invention are prepared in a manner which takes into account the higher reactivity of the 2'-hydroxy group over the hydroxy group in the 7-position of taxoids.

G. 2'- SUBSTITUTED TAXOIDS

2'- substituted taxoid derivatives can be prepared by reacting a taxoid with a reagent having the structure of Formula (IV):

wherein $R_1$, X and (n) are as previously defined and $R_2$ is a group capable of being displaced by a nucleophilic reagent. It is in this aspect of the invention that $R_1$ is preferably a polymer having a molecular weight of from about 20,000 to 80,000 as described above in Section D. $R_2$ is preferably selected from halides, N-hydroxysuccinimidyl (NHS), N-hydroxybenzotriazolyl, p-nitrophenoxy, imidazolyls and the like. As used herein, Formula (IV) is referred to a polymeric ester-forming reagent or a carbonate forming reagent. NHS is the preferred ester forming reagent; activated carbonates or acid chlorides are preferred carbonate forming reagents. Example 1 shows synthesis of a Formula (IV) reagent.

When X is NH, the reagent of Formula (IV) can be formed, for example, by first reacting glycine ethyl ester with PEG-chloride, followed by saponification, reaction with N-hydroxysuccinimide (NHS) in presence of dicyclohexylcarbodiimide (DCC).

The 2'-substitution reaction with the compounds of Formula (IV) is conducted in the presence of a inert organic solvent such as methylene chloride, toluene, tetrahydrofuran or DMSO and optionally in the presence of a base. The preferred bases are selected form the group consisting of tertiary amines such as triethylamine, diisopropylethylamine and pyridine. Pyridine may also serve as a solvent.

The reaction temperature should be below the decomposition temperature of taxol, preferably from about 4° C. to about 115° C., most preferable about 25° to 60° C. The reaction is preferably being conducted with a slight excess of the (Formula IV) acylating agent.

H. PROTECTING REAGENTS 7-substituted taxoids are prepared by reacting a starting taxoid derivative with a reagent capable of providing a protective group in the 2'- position. Protective reagents are shown as Formula (V):

wherein:

(X) is as defined above, (m) is a positive integer, preferably one;

$R_3$ is selected from lower alkyls having 1 to 4 carbon atoms, aryls, polyalkylene oxides and the like; and $R_4$ is a group capable of being displaced by a nucleophilic reagent such as those identified for $R_2$ of Formula (IV). One preferred protecting moiety is methoxy acetate (Mac). Reaction conditions for attaching the protecting group in the 2' position of the taxoid are the same as those set forth above in Section G. Alternatives to the protective reagents are simply those reagents of Formula (IV). This can be advantageous when the artisan seeks disubstituted taxoids.

I. 7-SUBSTITUTED TAXOIDS

Once the 2'- position of the taxoid has been protected or substituted, the 7-carbonate or 7-polymeric ester can be formed by reacting a 2'-protected taxoid with a Formula (IV) reagent. As was described earlier, when (n) of (IV) is zero, a 7-carbonate is formed. When (n) is an integer, a 7-polymeric ester, for example, is formed. The reaction conditions, solvents, etc. are the same as those identified above. An illustrative compound, 2'-Mac-7-substituted taxol is shown below:

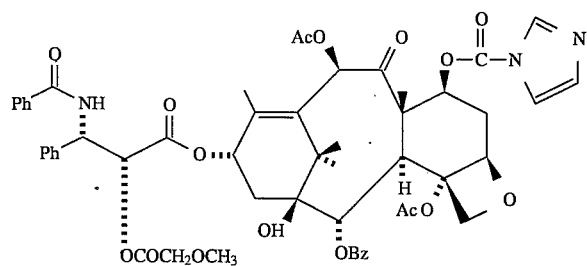

The resulting 2' protected taxoid is then reacted with a reagent of Formula (IV) to provide a 7-carbonate group or a 7-PAO ester. If desired, the 2'-protective group can be removed with an equivalent of a nucleophile such as a primary amine such as ethanolamine after the final 7 position modification has been carried out.

The 7-substituted taxoid derivatives can also be prepared by reacting a 2'- protected taxoid with e.g. phosgene, or derivative thereof such as triphosgene, carbonyl diimidazole or bis succinimidyl carbonate followed by reaction with an alcohol of the formula $R_1OH$ to replace the leaving group (Z) in the 7-position. See FIG. (VI) below as an illustration. (Z)=chlorine, carbonyl imidazole, succinimidyl carbonate, etc.; $R_1$ is the same as that described above.

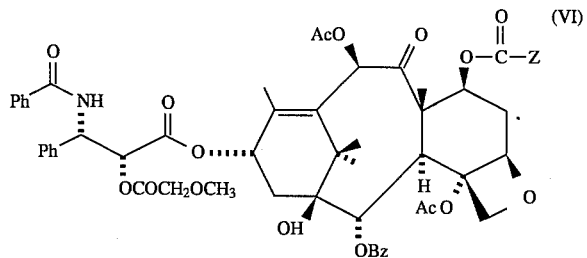

This intermediate is then reacted with an alcohol of the formula $R_1OH$ to replace the leaving group (Z). The protecting group in the 2' position and shown as (P) can also be removed as described above, if desired.

J. 2', 7 DISUBSTITUTED TAXOIDS bis-2', 7- disubstituted taxoid derivatives can be prepared by reacting a suitable taxoid with about 2 equivalents of a carbonate-forming or ester-forming reagent of Formula (IV) under the conditions set forth in section G. Alternatively, different moieties can be attached by first carrying out the 2' modification with one reagent of Formula (IV) and thereafter with a second Formula (IV) reagent for the 7- position modification.

K. METHODS OF TREATMENT

Another aspect of the present invention provides methods of treatment for various medical conditions in mammals. The methods include administering an effective amount of a modified taxoid which has been prepared as described herein to the mammal. The compositions are useful for, among other things, treating neoplastic disease, reducing tumor burden, preventing metastasis of neoplasms and preventing recurrences of tumor/neoplastic growths.

The amount of modified taxoid used in the treatment methods is generally described as that amount which effectively achieves the desired therapeutic result in mammals. Naturally, the dosages of the various modified taxoids will vary somewhat depending upon the taxoid moiety and the modifications made at the 2' and/or 7 position. In general, however, modified taxoid is administered in amounts ranging from about 5 to about 500 $mg/m^2$ per day, based the amount of the taxoid moiety in the conjugate. The range set forth above is illustrative and those skilled in the art will determine the optimal dosing of the conjugate selected based on clinical experience and the treatment indication.

The modified taxoid of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan.

EXAMPLES

The following examples serve to provide further appreciation of the invention but are not meant in any way to restrict the effective scope of the invention.

Example 1

Preparation of Peg-5000 N-Hydroxy Succinimide Active Ester

Potassium t-butoxide (1.7 g, 14.0 mmol) was added to 50 g (10 mmol) of dried methoxypolyethylene glycol (MW 5000) in toluene and stirred for 30 minutes. Ethyl bromoacetate (3.4 g, 20.0 mmol) was then added and the reaction mixture was refluxed for 24 hours. The reaction mixture was then evaporated to dryness, dissolved in methylene chloride, washed with water, dried over sodium sulfate and evaporated to dryness followed by recrystallization from 2-propanol. The PEG-ester thus obtained (48 g) was subjected to hydrolysis in 0.1M NaOH (500 ml) at room temperature for 5 hours. After acidification to Ph 5, the product was extracted with methylene chloride. After the workup as above, the product was recrystallized from 2-propanol (yield 44 g).

The PEG-acid obtained above (40 g, 8 mmol) was dissolved in 400 mL of methylene chloride and treated with diiso-propylcarbodiimide (1.51 g, 12 mmol) at 0° C. After 30 minutes, N-hydroxysuccinimide (1.84 g, 16 mmol) was added and stirred at room temperature for 3 hours. After the workup as above, the PEG-active ester was purified by recrystallization from 2-propanol and characterized by NMR and non-aqueous titrations.

Example 2

Preparation of 2'- Peg 5000 Ester Taxol

Taxol (25 mg, 0.029 mmol) was dissolved in 1 mL anhydrous pyridine in a sample tube. To this solution 300 mg (0.058 mmol) of the Peg-active ester prepared as above was added and the tube was securely capped. The tube was heated at 60° C. and the reaction was monitored by HPLC. When the reaction was more than 90% complete the reaction mixture was evaporated to dryness and purified by preparative HPLC (yield 60 mg). The product was characterized by NMR, IR and FAB-Mass spectra.

Example 3

Preparation of 7- Methyl Carbonate Taxol

The N-Hydroxysuccinimidyl ester of methoxyacetic acid (Mac-NHS) a Formula (IV) reagent, was prepared as follows: N-Hydroxysuccinimide (2.53 g, 22.0 mmol) was suspended in 10 mL of methylene chloride along with methoxyacetyl chloride (2.17 g, 20.0 mmol). Thereafter, a solution containing diisopropylethylamine (2.84 g, 22.0 mmol) in 15 mL of methylene chloride was added. After stirring at room temperature for 4 hours, the reaction mixture was washed with water, dried over sodium sulfate and evaporated to dryness. The crude product was recrystallized from 1:1 ethyl acetate-hexane(yield 2.4 g, 64%). The product was characterized by IR, NMR and elemental analysis.

Taxol 2'-methoxyacetate (2'-MAc-taxol) was prepared by heating taxol (100 mg, 0.117 mmol) with MAc-NHS (86 mg, 0.46 mmol) in 1 mL anhydrous pyridine at 60° C. until more than 99% of the taxol was converted to the product. 11 mg of methanol was added to the reaction mixture and after 15 minutes, dissolved in methylene chloride and subjected to the work up procedure as described above (yield 95 mg, 88%). The product was characterized by NMR and FAB-mass spectra.

Substitution of the 7-position was accomplished by treating 2'-MAc-taxol (50 mg, 0.054 mmol) with methyl chloroformate (26 mg, 0.28 mmol), and pyridine (22 mg, 0.28 mmol) in 1 mL anhydrous methylene chloride for 5 hours at 25° C. After extraction with water to remove excess reagent, ethanolamine (3.4 mg, 0.056 mmol) was added and stirred at room temperature overnight. After workup as above, taxol 7-methyl carbonate was obtained, which was characterized by NMR and FAB-Mass-spectra (yield 40 mg, 75%).

Example 4

Preparation of 2'-Peg 5000-Ester-7-Methyl Carbonate Taxol

Taxol 2'-Peg ester (30 mg, 0.005 mmol) prepared according to Example 2 was dissolved in 1 mL of methylene chloride and treated with methyl chloroformate (4.8 mg, 0.05 mmol) and pyridine (4 mg, 0.05 mmol). The reaction mixture was heated to 60° C. for 5 hours. After the workup described above, the crude product obtained was purified by recrystallization from 2-propanol (yield 21 mg, 70%). The product was characterized by NMR and FAB-Mass spectra.

We claim:

1. A taxane-based composition, comprising a moiety of the formula:

wherein:

n is a positive integer;

X is oxygen or NL, where L is selected from the group consisting of hydrogen, $C_{1-8}$ alkyls, aryls and aralkyls; and $R_1$ is selected from the group consisting of substantially nonantigenic polymers, $C_{1-12}$ alkyls and substituted alkyls.

2. The composition of claim 1, wherein X is oxygen.

3. The composition of claim 1, wherein n is 1.

4. The composition of claim 1, wherein said substituted alkyls comprise a member of the group consisting of hydroxy, amino, alkylthio, aryl and aralkyl moieties.

5. The composition of claim 1, wherein said substantially nonantigenic polymer is a polyalkylene oxide.

6. The composition of claim 5, wherein said polyalkylene oxide comprises an alkyl terminal.

7. The composition of claim 6, wherein said alkyl-terminated polyalkylene oxide is a monomethyl-terminated polyethylene glycol, (mPEG).

8. The composition of claim 1, wherein said substantially non-antigenic polymer has a molecular weight of from about 200 to about 10,000.

9. The composition of claim 8, wherein said substantially non-antigenic polymer has a molecular weight of from about 1,000 to about 7,500.

10. The composition of claim 9, wherein said substantially non-antigenic polymer has a molecular weight of from about 2,000 to about 5,000.

11. The composition of claim 1, wherein said polymer is selected form the group consisting of dextran, polyvinyl pyrrolidones, polyacryl amides, polyvinyl alcohols and carbohydrate-based polymers.

12. The composition of claim 1, wherein said taxane is substituted in the 7 position with a methyl carbonate moiety.

13. A method of preparing a taxane-based composition, comprising reacting a taxane of the formula

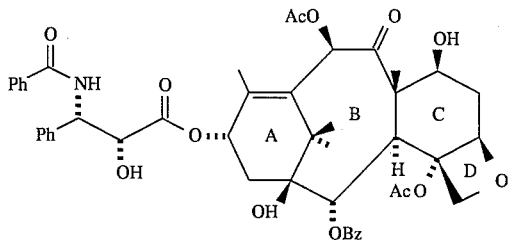

with a reagent of the formula:

$$R_1-X-(CH_2)_n-\overset{O}{\underset{\|}{C}}-R_2 \qquad (IV)$$

wherein:

n is a positive integer;

X is oxygen or NL, where L is selected from the group consisting of hydrogen, $C_{1-8}$ alkyls, aryls and aralkyls; and $R_1$ is selected from the group consisting of substantially nonantigenic polymers, $C_{1-12}$ alkyls and substituted alkyls and $R_2$ is a group capable of being displaced by a nucleophilic reagent and is selected from the group consisting of halides, N-hydroxysuccinimidyl, N-hydroxybenzotriazolyl, p-nitrophenoxy and imidazolyls whereby a composition of the formula:

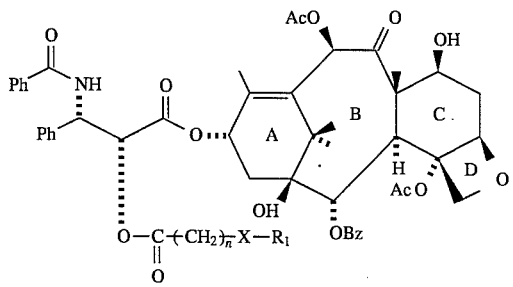

is produced.

14. The method of claim 13, wherein X is oxygen.

15. The method of claim 13, wherein n is 0 or 1.

16. The method of claim 13, wherein said substituted alkyls comprise a member of the group consisting of hydroxy, amino, alkylthio, aryl and aralkyl moieties.

17. The method of claim 16, wherein said substantially nonantigenic polymer is a polyalkylene oxide.

18. A method of treating a condition selected from the group consisting of neoplastic disease, tumor burden, neoplastic metastasis, recurrences of tumor growth and recurrences of neoplastic growth in mammals, comprising administering an effective amount of a taxane composition of claim 1.

19. The method of claim 18, wherein said taxane is substituted in the 7-position with a methyl carbonate moiety.

20. The method of claim 19, wherein said taxane is substituted in the 2'-position with a polymeric ester.

21. The composition of claim 1, wherein said substantially non-antigenic polymer has a molecular weight of from about 20,000 to about 80,000.

22. The composition of claim 21, wherein said substantially non-antigenic polymer has a molecular weight of from about 30,000 to about 50,000.

23. The composition of claim 22, wherein said substantially non-antigenic polymer has a molecular weight of from about 35,000 to about 45,000.

24. The composition of claim 5, wherein said polyalkylene oxide is a homobifunctional polyalkylene oxide, the alpha terminal thereof linked to X.

25. The composition of claim 24, wherein the omega terminal of said polyalkylene oxide is linked to a taxane.

26. A taxane-based composition, comprising a moiety of the formula:

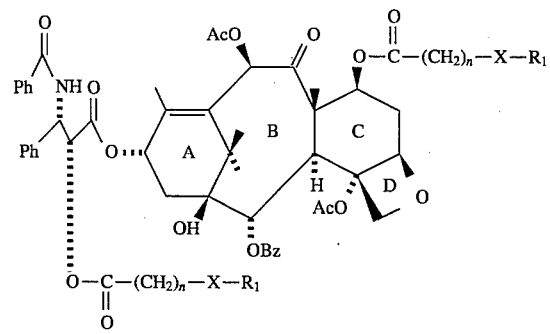

wherein:

n is a positive integer for the 2'-position substitution and independently zero or a positive integer for the 7-position substitution;

each X is independently oxygen or NL, where L is selected from the group consisting of hydrogen, C1-8 alkyls, aryls and aralkyls; and each $R_1$ is independently selected from the group consisting of substantially nonantigenic polymers, $C_{1-12}$ alkyls and substituted alkyls.

27. A taxane-based composition, comprising a moiety of the formula:

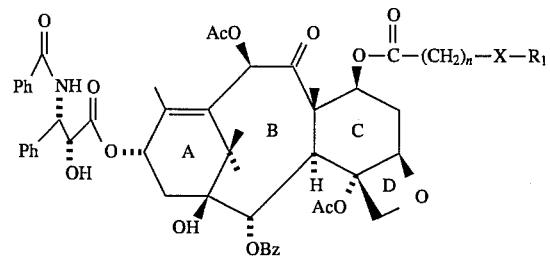

wherein:

n is zero or a positive integer;

X is oxygen or NL, where L is selected from the group consisting of hydrogen, $C_{1-8}$ alkyls, aryls and aralkyls; and $R_1$ is selected from the group consisting of substantially nonantigenic polymers, $C_{1-12}$ alkyls and substituted alkyls;

except that X is not NH when n is zero.

* * * * *